United States Patent
Jurado et al.

(10) Patent No.: US 8,640,525 B2
(45) Date of Patent: Feb. 4, 2014

(54) METHODS AND SYSTEMS FOR DIFFERENTIATING SOYBEANS

(75) Inventors: Luis A. Jurado, St. Louis, MO (US); Joel E. Ream, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 355 days.

(21) Appl. No.: 12/978,977

(22) Filed: Dec. 27, 2010

(65) Prior Publication Data

US 2011/0154882 A1   Jun. 30, 2011

Related U.S. Application Data

(60) Provisional application No. 61/291,104, filed on Dec. 30, 2009.

(51) Int. Cl.
*G01N 33/00* (2006.01)

(52) U.S. Cl.
USPC ........................................ 73/23.34

(58) Field of Classification Search
USPC .................. 73/23.2, 23.34; 422/83
See application file for complete search history.

(56) References Cited

U.S. PATENT DOCUMENTS

| | | | |
|---|---|---|---|
| 6,435,002 B1 * | 8/2002 | Briggs ........................... | 73/23.2 |
| 2002/0023480 A1 * | 2/2002 | Hattori et al. ................ | 73/31.05 |
| 2005/0287234 A1 * | 12/2005 | Sakata et al. .................. | 424/757 |
| 2008/0219891 A1 * | 9/2008 | McDevitt et al. .......... | 422/82.05 |
| 2009/0068337 A1 | 3/2009 | Bringe et al. | |

FOREIGN PATENT DOCUMENTS

WO   2007030429 A2   3/2007

OTHER PUBLICATIONS

Chandra, M. Jeya, Statistical Quality Control, 2001, CRC Press, pp. 1-3.*
Antihus Hernández Gómez, et al., Evaluation of Tomato Maturity by Electronic Nose, ScienceDirect, Computers and Electronics in Agriculture, 2006, vol. 54, pp. 44-52, Elsevier B. V.
F. Korel, et al., Ground Red Peppers: Capsaicinoids Content, Scoville Scores, and Discrimination by an Electronic Nose, Journal of Agricultural and Food Chemistry, 2002, vol. 50, pp. 3257-3261, American Chemical Society.
F. Korel, et al., Capsaicin and Dihydrocapaiscin Composition of Turkish Red Peppers Determined by High Pressure Liquid Chromatography and Correlated with an Electronic Nose, Institute of Food Technologists Annual Meeting, 2000, 86G-3, 2 Pages.
F. Maul, et al., Tomato Flavor and Aroma Quality as Affected by Storage Temperature, Journal of Food Science, Sensory and Nutritive Qualities of Food, 2000, vol. 65, No. 7, pp. 1228-1237, Institute of Food Technologists.
Pavithra N. Raj, et al., Quality Assessment of Oil Blends by Electronic Nose Technique and Sensory Methods, Journal of Sensory Studies, 2006, vol. 21, pp. 322-332, Department of Sensory Science Central Food Technological Research Institute, Blackwell Publishing.

(Continued)

*Primary Examiner* — Hezron E Williams
*Assistant Examiner* — David Z Huang
(74) *Attorney, Agent, or Firm* — Armstrong Teasdale LLP

(57) ABSTRACT

Methods and systems for analyzing soybeans and, more particularly, for analyzing soybeans at the point of delivery such as a grain elevator or processing plant for a characteristic of the soybeans such as the β-conglycinin protein content or the intensity of flavor of the soybeans.

20 Claims, 9 Drawing Sheets

(56) References Cited

OTHER PUBLICATIONS

Schnitzler, W.H., et al., Characterization of Internal Quality of Vegetables by Headspace Gaschromatography and "Electronic Nose," Institute for Vegetable Science, Technische Universtität München, 2000, Proc. XXV 1HC—Part 7, Acta Hort. 517, pp. 361-368, Ed. M. Herregods, Germany.

H.L. Gan, et al., Characterisation of Vegetable Oils by Surface Acoustic Wave Sensing Electronic Nose, ScienceDirect, Food Chemistry, 2005, vol. 89, pp. 507-518, Elsevier Ltd.

FOX Electronic Nose, Alpha M.O.S., 1 Page, 2009.

Luis Jurado, The Application of Electronic Nose for Edible Oil Analysis, Presentation to the Institute of Food Technologists, Monsanto Company, 2007, 13 Pages.

Shin Nakamura et al., Molecular Biomedical Evaluation in Monkeys of Efficacy of Soy Products, Soy Protein and Soy Isoflavone for Treatment of Hypercholesterolemia (Part I), Soy Protein Research, 2004, vol. 7, pp. 13-19.

Shin Nakamura et al., Efficacy of Soy Product, Soy Protein or Soy Isoflavone, to Hypercholesterolemia and Osteoporosis: Its Molecular Biomedical Studies in Monkeys (Part II), Soy Protein Research, 2005, vol. 8, pp. 1-7.

Tatsuya Moriyama et al., Soybean β-Conglycinin Diet Suppresses Serum Triglyceride Levels in Normal and Genetically Obese Mice by induction of β-Oxidation, Downregulation of Fatty Acid Synthase, and Inhibition of Triglyceride Absorption, Biosci. Biotechnol. Biochem., 2004, vol. 68, pp. 352-359.

Michael R. Adams et al., Dietary Soy β-Conglycinin (7S Globulin) Inhibits Atherosclerosis in Mice 1,2, J. Nutr., vol. 134, 2004, pp. 511-516, American Society for Nutritional Sciences.

Toshimitsu Baba et al., Effects of Soybean β-Conglycinin on Body Fat Ratio and Serum Lipid Levels in Healthy Volunteers of Female University Students, Food Science Research Institute, Department of Health Science, 2004, vol. 50, pp. 26-31.

Mitsutaka Kohno et al., Decreases in Serum Triacylglycerol and Visceral Fat Mediated by Dietary Soybean β-Conglycinin, Food Science Research Institute, Sumitomo Hospital, Emeritus Professor of Kyoto Univ., 2006, vol. 13, No. 5, pp. 247-255, Journal of Atherosclerosis and Thrombosis.

Wei-Yong Zuo, et al., Separation of growth-stimulating peptides for *Bifidobacterium* from soybean conglycinin, World Journal of Gastroenterology, 2005, vol. 11, No. 37, pp. 5801-5806, The WFG Press and Elsevier, Inc.

PCT International Search Report and Written Opinion of the International Searching Authority mailed on Mar. 17, 2011 regarding PCT/US2010/062141 filed on Dec. 27, 2010, 11 pages.

Monika Hirschfelder et al., Rapid Discrimination of Strawberry Varieties Using a Gas Sensor Array, Gartenbauwissenschaft, Jul. 1, 1998, pp. 185-190, vol. No. 4, Verlag Eugen Ulmer GmbH & Co., Stuttgart.

R. Infante et al., Quality oriented fruit breeding: Peach [*Prunus persica* (L.) Batsch], Journal of Food, Agriculture & Environment; 2008, pp. 342-356, vol. 6, No. 2.

Jeno Bernath et al., Evaluation of Selected Oregano (*Origanum vulgare* L. subsp. *hirtum letswaart*) Lines with Traditional Methods and Sensory Analysis, Journal of Herbs, Spices & Medicinal Plants, Jan. 1, 2005, pp. 19-26, vol. 11(4), The Haworth Press, Inc.

Alphus D. Wilson et al., Appilcations and Advances in Electronic-Nose Technologies, Sensors, Jun. 29, 2009, pp. 5099-5148, vol. 9.

Supriyadi et al., Maturity discrimination of snake fruit (*Salacca edulis* Reinw.) cv. Pondoh based on volaties analysis using an electonic nose device equipped with a sensor array and fingerprint mass spectrometry, Flavour and Fragrance Journal, 2004, pp. 44-50, vol. 19, Published online in Wiley InterScience (www.interscience.wiley.com).

A. Jonsson et al., Electronic nose for microbial quality classification of grains, International Journal of Food Microbiology, 1997, pp. 187-193, vol. 35, Elsevier.

\* cited by examiner

METHODS AND SYSTEMS FOR DIFFERENTIATING SOYBEANS

CROSS-REFERENCE TO RELATED APPLICATION

This application claims the benefit of U.S. Provisional Application No. 61/291,104, filed Dec. 30, 2009, which is incorporated herein by reference in its entirety.

BACKGROUND

The field of this disclosure relates to methods and systems for analyzing soybeans and, more particularly, to methods and systems for differentiating varieties of soybeans based on a characteristic of the soybeans.

Advances in biotechnology and crop science have allowed for expression of certain phenotypes in agricultural commodities such as soybeans. These advances have resulted in various soybean varieties including those with high oil, low linoleic acid content, that contain certain fatty acids such as docosahexaenoic acid or stearidonic acid or even soybean varieties that are high in β-conglycinin protein.

Soybeans with high levels of β-conglycinin protein have recently been found to be advantageous. β-conglycinin protein has been found to influence soybean odor and the odor of the resulting products with lower amounts of β-conglycinin protein corresponding to greater odor. β-conglycinin also influences the solubility of the soybean compositions in food beverages with higher amounts of β-conglycinin resulting in smoother and more consistent beverages.

β-conglycinin is also believed to positively impact human health (Baba et al., J. Nutr. Sci. Vitaminol., 50(1):26-31 (2004)). In particular, β conglycinin has been found to lower cholesterol, triglycerides and visceral fat. Kohno et al. demonstrated a significant reduction in triglyceride levels and visceral fat in human subjects that consumed 5 grams of β-conglycinin per day (Kohno et al., J Atheroscler Thromb, 13: 247-255, (2006)). Similarly, Nakamura et al. found that β-conglycinin upregulates genes associated with lipid metabolism in a primate model and found that β-conglycinin had a significant effect in preventing bone mineral density loss (Nakamura et al., Soy Protein Res. 8: 1-7 (2005)). In addition, β-conglycinin demonstrated effects in lowering serum insulin and blood sugar (Moriyama et al., Biosci. Biotechnol. Biochem., 68(2):352-359 (2004)). Due to β-conglycinin effects on triglycerides, cholesterol, fat, insulin and sugar levels, it may play an important role in health programs. In addition, β-conglycinin inhibits artery plaque formation in mice and may similarly affect human subjects as well (Adams et al., J. Nutr., 134(3):511-516 (2004)).

β-conglycinin may also significantly affect intestinal microflora in humans. β-conglycinin inhibits growth of harmful bacteria, such as *E. coli*, while stimulating growth of beneficial bacteria, such as bifidobacteria, in a number of animal models (Nakamura et al., Soy Protein Res 7: 13-19, 2004; Zuo et al., World J Gastroenterol 11: 5801-5806 (2005)). β-conglycinin could be used both to reduce *E. coli* growth after infection and maintain a healthy intestinal microbial community.

Soybean varieties high in β-conglycinin content include those described in International Pub. No. WO 2007/030429 and U.S. Pat. Pub. No. 2009/0068337, each of which is incorporated herein for all relevant and consistent purposes. Soybean varieties high in β-conglycinin content (often referred to as "HBC" varieties) may contain β-conglycinin in an average amount of from about 30% to about 40% by weight of the total soybean content of the soybeans or even from about 30% to about 50% by weight of the total soybean content of the soybeans. In contrast, varieties not designed or bred for high β-conglycinin content (which may be referred to herein as "commodity soybeans") contain β-conglycinin in an average amount less than about 30% or even less than about 25% by weight of the total soybean content of the soybeans.

Soybeans high in β-conglycinin content may be processed separately from commodity soybeans to take advantage of the β-conglycinin content of the soybeans (e.g., for incorporation into nutritional formulas and other beverages). Conventional methods of differentiating soybeans with relatively high β-conglycinin content involve gel electrophoresis (e.g., SDS-PAGE analysis) of soybean protein crude extracts. Gel electrophoresis techniques are not practical for differentiating soybeans at the point of grain delivery because these techniques are too labor-intensive and time-consuming.

Furthermore, it is desirable to differentiate soybeans that are low in odor or aroma from more odorous varieties so that the low-flavored varieties may be incorporated in beverages and the like for human consumption. Conventional flavor differentiation techniques involve gas chromatography-mass spectrometry, which is not practical because it is too complex and expensive. A continuing need exists for new methods and systems for differentiating soybean varieties that contain high-amounts of β-conglycinin and/or a low amount of odor or aroma and, particularly, methods that are simple to perform and provide results quickly making them suitable for use at the point of grain delivery (e.g., at grain elevators or processing plants).

SUMMARY

In one aspect of the present disclosure, a method for differentiating soybeans includes heating a sample of soybeans to release one or more volatile compounds from the soybeans. The volatile compounds are sensed to generate one or more electronic signals. The electronic signals are analyzed to determine a characteristic of the soybeans.

Another aspect of the present disclosure is directed to a method of determining the relative amount of β-conglycinin protein in a sample of soybeans. The sample of soybeans is heated to release one or more volatile compounds from the soybeans. The volatile compounds are sensed to generate one or more electronic signals. The electronic signals are processed to determine whether the sample of soybeans contains β-conglycinin protein in a concentration greater than commodity soybeans.

In a further aspect of the present disclosure, a method of determining the relative intensity of odor of a sample of soybeans includes heating the sample of soybeans to release one or more volatile compounds from the soybeans. The volatile compounds are sensed to generate one or more electronic signals. The electronic signals are processed to determine whether the sample of soybeans is less odorous than commodity soybeans.

Yet another aspect of the present disclosure is directed to a system for determining the relative amount of β-conglycinin protein in a sample of soybeans. The system includes a sensor and a processor. The sensor generates one or more electronic signals in response to contact with a gaseous compound. The processor is configured to analyze the electronic signals and determine the amount of β-conglycinin protein in the sample of soybeans.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

BRIEF DESCRIPTION OF THE DRAWINGS

Corresponding reference characters indicate corresponding parts throughout the drawings.

DETAILED DESCRIPTION

Figure 1:
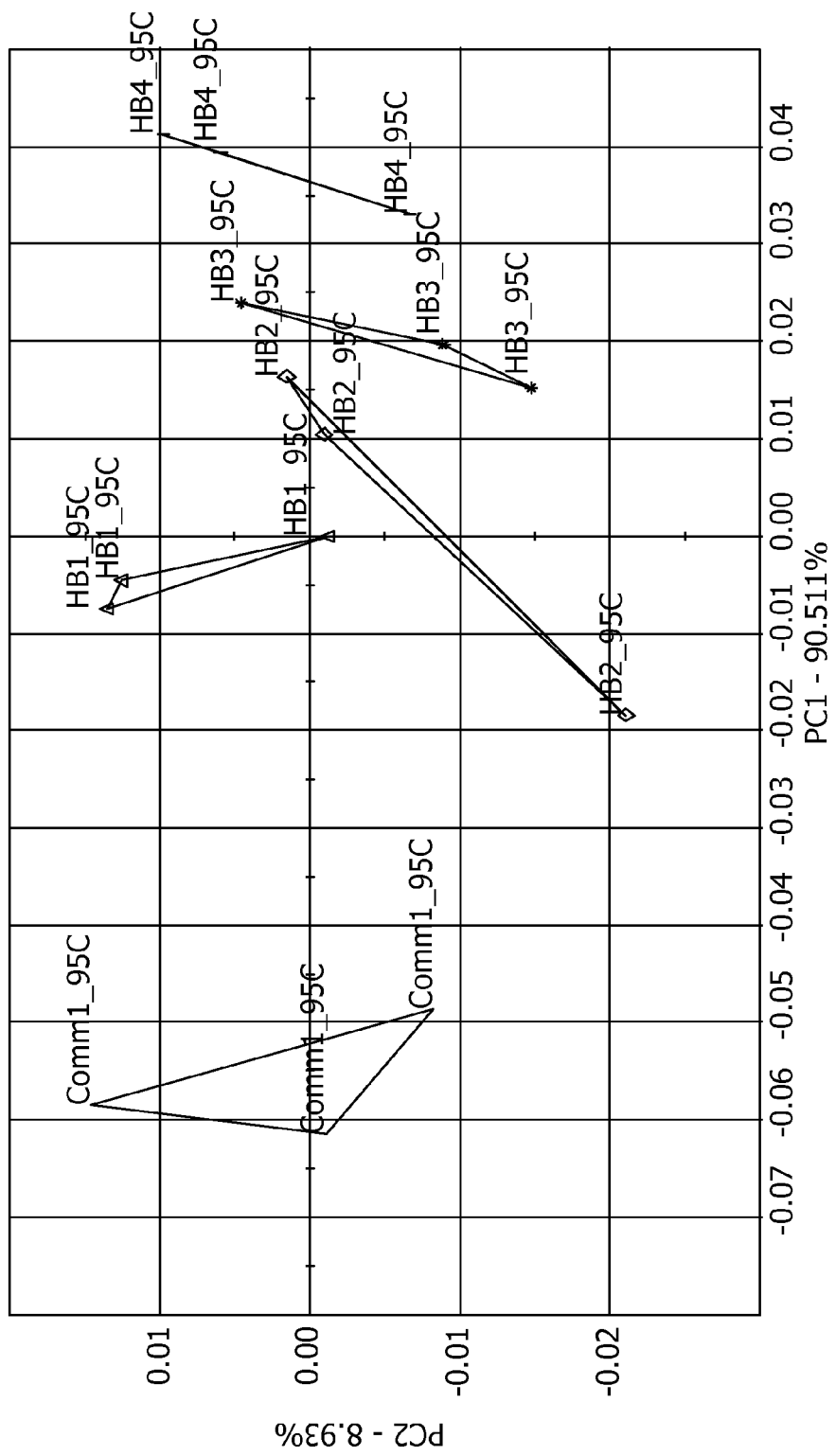
FIG. 1 is a graph of the principal component analysis (PCA) of a sample of whole soybeans heated to 95° C. and analyzed according to Example 1.

In accordance with the present disclosure, methods for differentiating soybeans are provided. While the methods and systems described herein are generally described with reference to differentiation of soybeans having a high β-conglycinin content or low odor compared to typical commodity soybeans, it should be understood that the methods and systems may be applied to differentiate soybeans having other characteristics without limitation. These other characteristics include, for example, the genetic line, variety, composition, moisture content, odor intensity, spoilage, gene expression, oil content, fatty acid profile, linoleic acid content, protein content, chlorophyll content, oxidation and combinations thereof.

In various embodiments of the present disclosure, a sample of soybeans is provided for analysis. Soybeans may be sampled from a batch taken from soybeans delivered for processing or for storage. Automated sampling probes may be employed to gather the sample from the respective shipment container (e.g., truck, railcar, barge and the like). Several samples may be gathered from one respective shipment and each individual sample may be analyzed or, alternatively, the samples may be combined to provide a composite sample that is analyzed. In this regard, the analysis techniques described herein are capable of analyzing relatively small samples such as sample sizes of less than about 10 g (e.g., from about 0.1 g to about 10 g). Sampling techniques other than as described may be used without departing from the scope of the present disclosure.

The sample of soybeans may be processed to release volatile components from the soybeans. For example, the soybeans may be ground to reduce their particle size and to expose inner portions of the soybean to the atmosphere. The soybean may be ground to a powder consistency (e.g., using a ball mill). The soybeans (either whole or after grinding) may be added to a solvent. The solvent may promote vaporization of volatile components. One or more compounds present within the soybean material may dissolve in the solvent and then vaporize from the solution into the headspace above the solution. It should be noted that the terms "solvent" and "solution" should not be viewed in a limiting sense. For example, a portion of the soybeans (particularly the fiber portions) may not dissolve into the solvent, but rather become suspended throughout the solvent. Suitable solvents include various buffer solutions and water. The pH of the buffer solutions may be from about 4.5 to about 9 or from about 5 to about 8. The buffer solutions may be aqueous and/or may contain salts such as NaCl or $CaCl_2$ and may contain EDTA. The mass ratio of soybeans to solvent may be at least about 1:10, at least about 1:5, at least about 1:3, at least about 1:1 or even higher with ratios of at least about 2:1, at least about 5:1 or even at least about 10:1 (e.g., from 1:10 to 2:1 or from about 1:5 to about 1:1) being suitable. In this regard, it should be understood that soybeans that have not been ground (i.e., whole soybeans) and not contacted with a solvent may be analyzed in accordance with the methods and systems of the present disclosure (see Example 1).

While typically the entire sample of soybeans (either whole or in solvent) is heated and analyzed for volatiles, one or more portions of the soybean may be isolated for analysis. As an example, soybean oil may be extracted from a sample of soybeans and the oil may be analyzed (typically with heating) to determine a characteristic of the soybeans to determine the fatty acid profile of the soybeans (e.g., whether the soybeans are a low-linoleic acid variety). Low-linoleic acid soybean varieties produce distinct volatile compounds or a distinct concentration of volatile compounds that may be sensed and analyzed to determine whether the soybeans are a low-linoleic acid variety.

The soybeans (including whole soybeans or solutions) may be heated to further release volatile compounds. In some embodiments, the sample of soybeans is heated to a temperature of at least about 30° C., at least about 40° C., at least about 50° C., at least about 60° C. at least about 70° C., at least about 80° C., at least about 90° C., at least about 100° C. or from about 30° C. to about 150° C., from about 30° C. to about 110° C., from about 45° C. to about 110° C. or from about 50° C. to about 100° C. The sample of soybeans may be heated for at least about 30 seconds to vaporize volatile compounds and, in other embodiments is heated at least about 1 minute, at least about 5 minutes, at least about 15 minutes or from about 30 seconds to about 1 hour, from about 30 seconds to about 30 minutes or from about 5 minutes to about 30 minutes. While the above-referenced temperatures and periods of heating are typical for the methods of analysis described herein, other temperatures and/or periods of heating may be used without departing from the scope of the present disclosure.

Generally, the soybeans are heated in an enclosed container having a headspace in which volatile compounds released from the soybeans may collect. The headspace into which the volatile compounds enter may be air including purified air; however, it should be understood that other gases may be used without departing from the scope of the present disclosure.

Air may be purified by removing volatile compounds therefrom and according to methods known in the art such as by, for example, membrane filtration. After the sample has been heated for the pre-determined time period, a volume of gas in the headspace containing the volatile compounds may be injected into a sensor for analysis. The volume of gas injected into the sensor for analysis may vary and in some embodiments is at least about 0.1 ml, at least about 0.5 ml, at least about 1 ml, at least about 2 ml or from about 0.1 ml to about 5 ml. A pump or blower may be used to pull or push the volatile compounds from the headspace of the container to the sensor to allow the volatile compounds to contact the sensing elements. Optionally, a valve (referred to as "23" in FIG. 9) may be used to hold the components in the headspace of the container during generation of vaporized compounds (i.e., the valve is closed during this step). The valve may then be opened to release the volatile components and to allow them to contact the sensing elements of the sensor with or without use of a pump. In some embodiments, the sensing elements themselves are located in the headspace of the container and/or the sensing system is configured to allow volatile compounds to travel to the sensing elements by diffusion. Purified air may be used to establish baseline measurements and to desorb volatiles that contact the sensing elements.

As stated above, the sensor may be configured to determine the $\beta$-conglycinin content of the soybean sample and/or the content relative to commodity soybeans which do not contain an elevated amount of $\beta$-conglycinin. In this regard, it should be understood that the $\beta$-conglycinin content is not determined directly; rather compounds such as hexanals, aldehydes, ketones, alcohols and the like are released from the soybeans and sensed by the sensors. Without being bound to a particular theory, it is believed that these compounds are released as oxidation or decomposition products of enzymatic or decomposition reactions upon heating the soybeans. The electronic signals produce a "fingerprint" that may be used to determine the $\beta$-conglycinin content of the soybean sample and/or the content relative to commodity soybeans.

The sensors may also be configured to measure or determine the odor (or synonymously "aroma," "flavor" or "odor intensity") and/or the odor relative to commodity soybeans. In other embodiments, the characteristic of the soybeans that is analyzed is a characteristic other than $\beta$-conglycinin content or odor such as, for example, the genetic line or variety of the soybeans, the composition or moisture content of the soybeans, or the odor intensity, spoilage, gene expression, oil content, fatty acid profile, linoleic acid content, protein content, chlorophyll content, oxidation or combinations thereof.

Sensors for detecting volatile compounds and for differentiating the types and concentrations of compounds produced by soybeans high in $\beta$-conglycinin content from that of commodity soybeans may contain one or more sensing elements. A number of different types of sensing elements may be used, including, for example, polymers, metal oxides, quartz crystals, surface acoustic wave sensors and optical fibers. In one or more embodiments, a plurality of sensing elements may be arranged as an array to detect volatile components. Each sensing element produces an electronic signal in response to contact with a volatile component so as to produce a "fingerprint" of signals which can be compared to stored data to determine the amount (or relative amount) of $\beta$-conglycinin in a sample of soybeans. The amount of sensors in the array may range from about 2 to about 50 or more (e.g., from about 10 to about 20).

When polymers are used as sensing elements, the polymer material may be conducting and/or may swell or contract upon contact with certain compounds. Typically each element of the array of polymers is distinct from other members of the array. For instance, the polymers may differ in their type of monomer subunits, concentration of electrically conductive dopant or the like. When metal oxides are used, the metal oxides may be part of a metal oxide semiconductor ("MOS") or even a field-effect transistor ("MOS-FET").

It should be noted that the electronic signals generated by the sensors may simply be a digital value or a measurement such as voltage or the conductance signal. Generally, contact of the sensors with a volatile components elicits a change in the electrical resistance resulting in a change in voltage. The change in resistance depends on the characteristics of the sensors (coatings, dopants and the like) and the volatile component or components that contact the sensor. In this regard, the term "electronic signal" should not be viewed in a limiting sense. Further, it should be understood that the volatile components that contact the sensor may be but typically are not the same compounds of interest. For example, it is believed that soybeans high in $\beta$-conglycinin content contain certain enzymes that generate one or more compounds that are released as volatiles that contact the sensor and that these volatiles are not generated, or are generated in a lesser concentration, in varieties that do not contain an elevated amount of $\beta$-conglycinin protein.

Upon generation of the electronic signals, the signals are analyzed to determine whether the soybeans have one or more characteristics such as elevated $\beta$-conglycinin content. In some embodiments, the sensor may be previously calibrated such that the electronic signals are correlated to an amount of $\beta$-conglycinin in the sample of soybeans. Calibration may be performed by processing a sample of soybeans with a known $\beta$-conglycinin content (e.g., as determined by SDS-PAGE analysis) in the analysis system to generate electronic signals which may be related to the $\beta$-conglycinin content. In one or more embodiments, the system is calibrated by determining a set of parameters in which the soybeans from which the soybean sample is gathered are considered to be "conforming" (see Examples 1-2 below). This allows soybean samples to be analyzed with the output of the analysis being whether the soybeans contain a minimum or maximum characteristic such as a minimum $\beta$-conglycinin content that is above that of commodity soybeans. This allows out-of-specification shipments to be rejected at the point of grain delivery. In addition or alternatively, the electronic signal fingerprint may be analyzed by known statistical techniques. For instance, the electronic signals may be analyzed by principal component analysis ("PCA") or by a statistical quality control model ("SQC").

Figure 9:
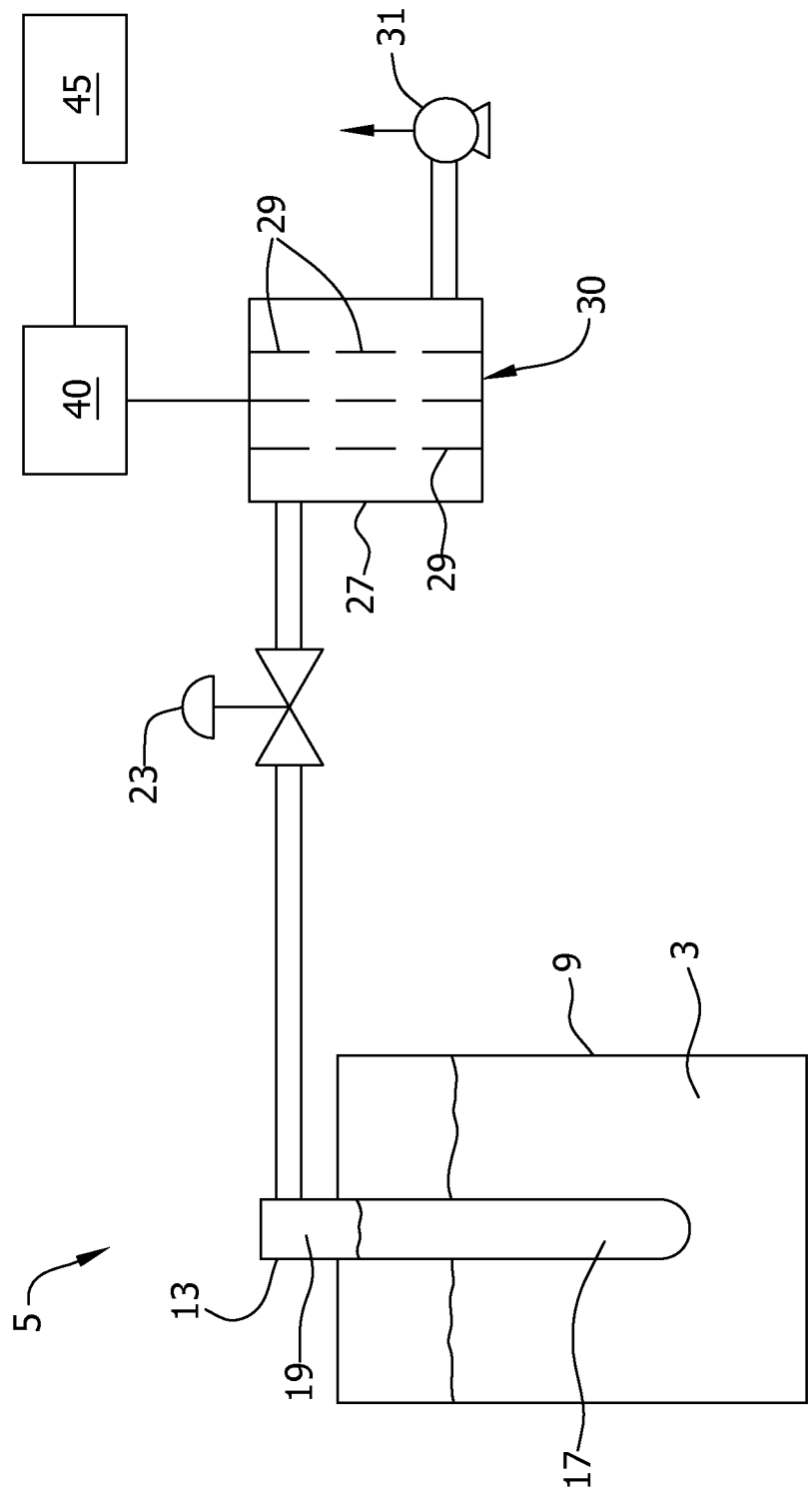
FIG. 9 is a schematic of a system for differentiating soybeans according to one embodiment of the present disclosure with a processor and memory unit shown in schematic.

The methods of the present disclosure may be performed by operation of a system for determining a characteristic (e.g., the relative amount of $\beta$-conglycinin protein) of a sample of soybeans. An exemplary system is shown in FIG. 9 with the system being generally designated as numeral 5. The system 5 generally includes a container 13 in which a sample of soybeans 17 (optionally in a solvent) are heated. The container 13 has a headspace 19 in which volatile compounds released from the soybeans 17 may collect.

The system 5 may also include a heating element 9 for heating the sample of soybeans. For instance, the container 13 containing the sample of soybeans may be at least partially immersed in a hot bath 3 (as shown in FIG. 9) to vaporize volatile compounds. Alternatively, hot gases may be directed against the container 13 to vaporize the volatile compounds. Suitable methods for heating include, without limitation, capacitive heating, induction coils (RF) and electrical resistance elements.

The system 5 also includes a sensor 30 to generate one or more electronic signals in response to receiving, contacting or sensing a gaseous compound. The system 5 also includes a processor 40 configured to analyze the electronic signals and provide information concerning a characteristic of the soybeans such, for example, the amount of β-conglycinin protein in the sample of soybeans. The sensor 30 may include a housing 27 and one or more sensing elements 29 within the housing. The sensing elements 29 (and optionally an array of elements as shown in FIG. 9) of the sensor 30 may be selected from polymers, metal oxides, quartz crystal, surface acoustic wave sensors, optical fiber sensors and combinations thereof as described above. A pump 31 may convey the volatile compounds from the headspace 19 of the container 13 into the housing 27.

The system 5 may also include a memory unit 45 in which a library of data is stored. The library of data may relate to the β-conglycinin protein content of soybeans and/or to typical patterns of electronic signals produced upon analyzing a sample of soybeans that contain an average or elevated amount of β-conglycinin protein.

While the system 5 shown in FIG. 9 includes a container for heating and analyzing one sample, it should be understood that several samples may be processed and/or analyzed simultaneously without departing from the scope of the present disclosure. For instance, a plurality of samples may be included within a plurality of processing wells of a sample system and processed in parallel. Other methods and systems for differentiating soybeans other than as described and shown may be used and the illustrations and descriptions of the present disclosure should not be viewed in a limiting sense.

EXAMPLES

Example 1

Differentiation of Soybean Varieties without Grinding or Use of a Solvent

Figure 2:
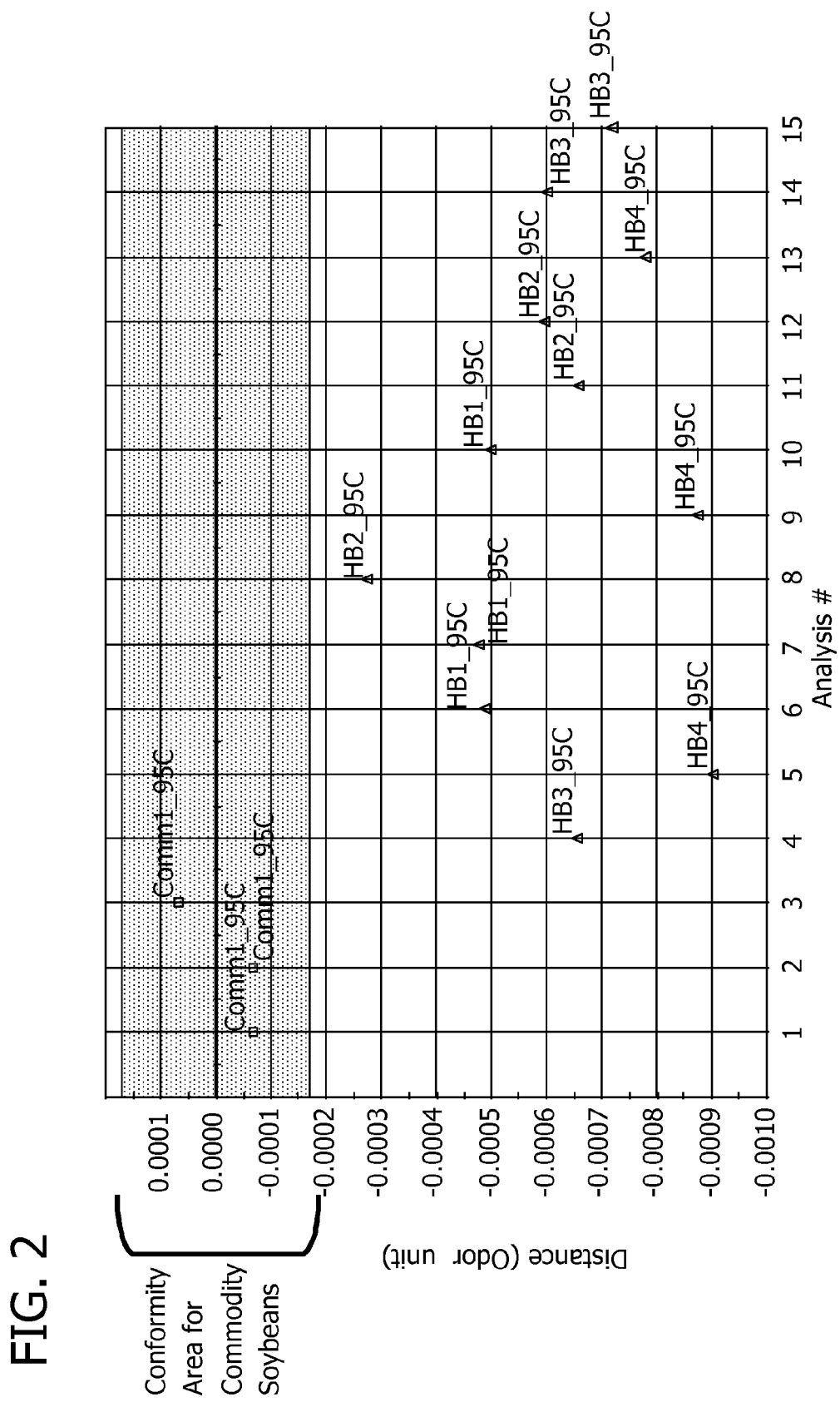
FIG. 2 is a graph of the statistical quality control (SQC) analysis of a sample of whole soybeans heated to 95° C. and analyzed according to Example 1.

Samples of four different varieties of soybeans were obtained. One variety was a typical commodity type soybean and the other three were high β-conglycinin varieties. The commodity soybean also had more odor (i.e., flavor) than the high β-conglycinin varieties. A sample of whole soybeans of each variety (1±0.05 g) was placed in a respective 10 ml amber glass vial that was sealed. The soybeans were heated to 95° C. for 20 minutes. 2.5 ml of headspace above the sample was injected into a sensor for analysis. The sensor was a Fox 4000 electronic nose system (Alpha MOS; Toulouse, France) using 18 MOS sensing elements. The PCA analysis of the samples heated to 95° C. is shown in FIG. 1 and the SQC analysis of the samples heated to 95° C. is shown in FIG. 2. As can be seen in FIGS. 1 and 2, the commodity soybeans (labeled "Comm1_95C") are grouped separate from the soybean varieties high in β-conglycinin content (labeled "HB195C," "HB2_95C" and "HBC_95C") This indicates that it is possible to distinguish high β-conglycinin content varieties from other varieties with lower amounts of β-conglycinin and varieties high in aroma from varieties with relatively lower aroma.

Example 2

Differentiation of Soybean Varieties with Grinding and Use of a Solvent

Figure 3:
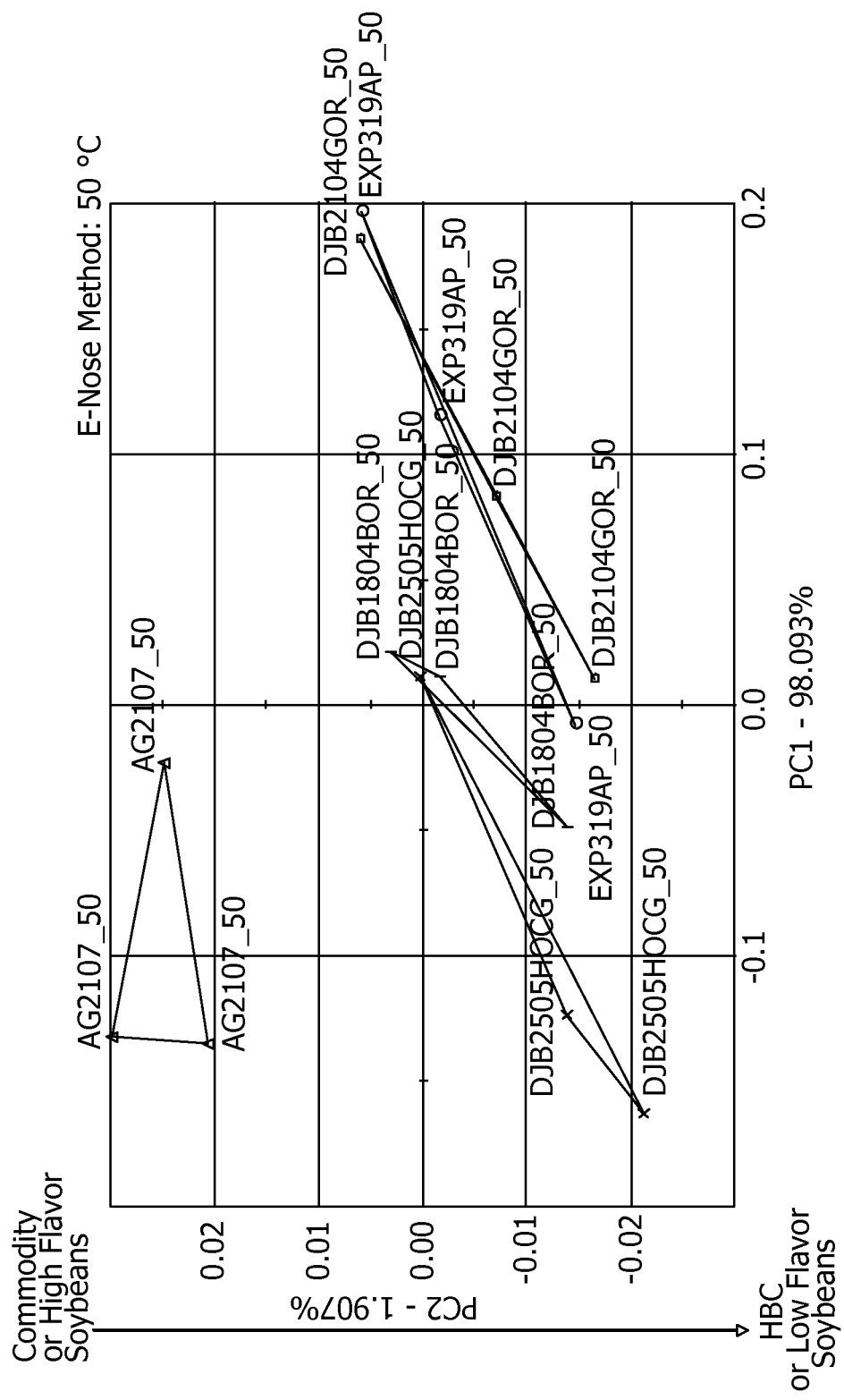
FIG. 3 is a graph of the PCA analysis of a sample of ground soybeans in water heated to 50° C. and analyzed according to Example 2.
Figure 4:
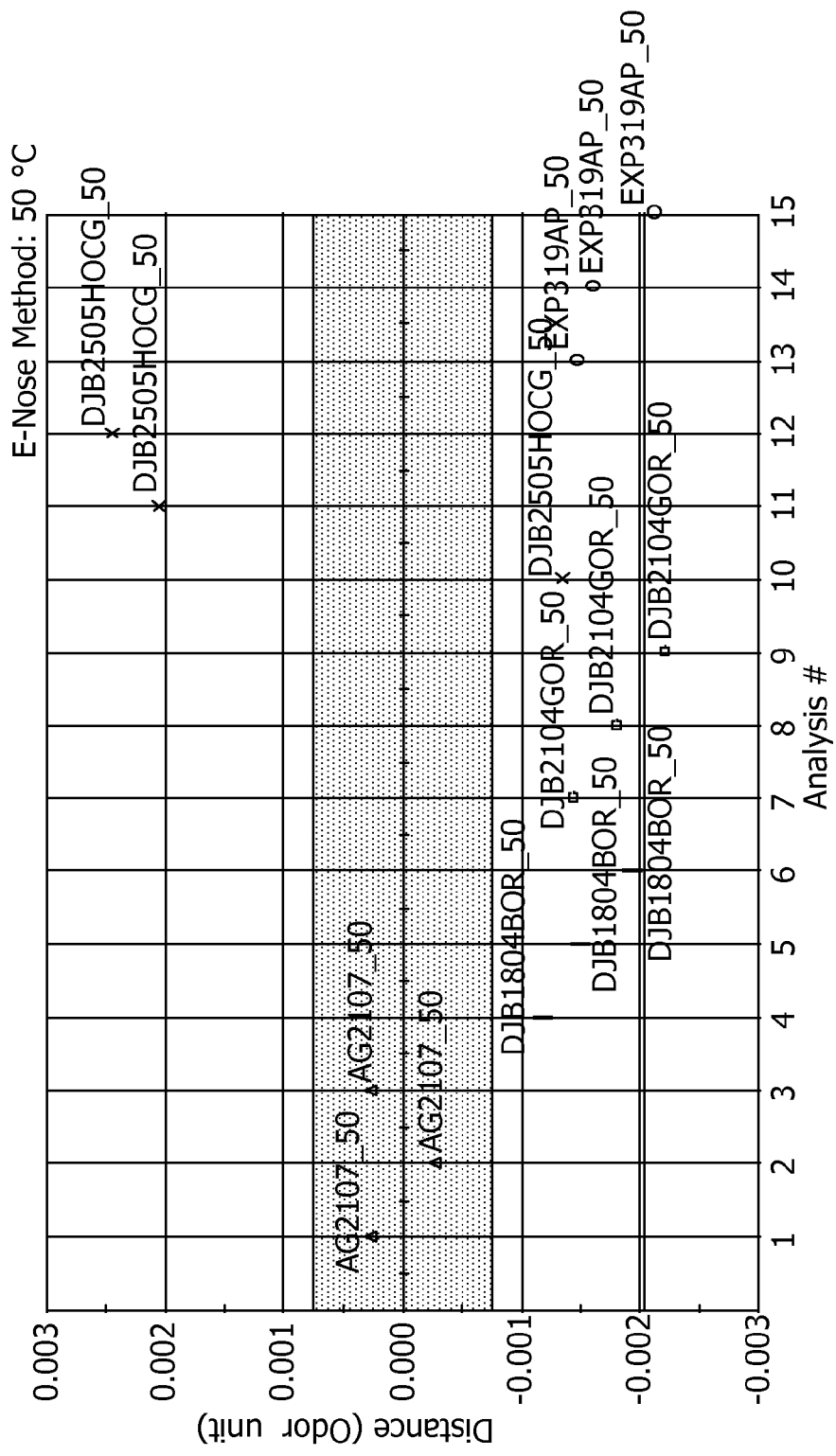
FIG. 4 is a graph of the SQC analysis of a sample of ground soybeans in water heated to 50° C. and analyzed according to Example 2.
Figure 5:
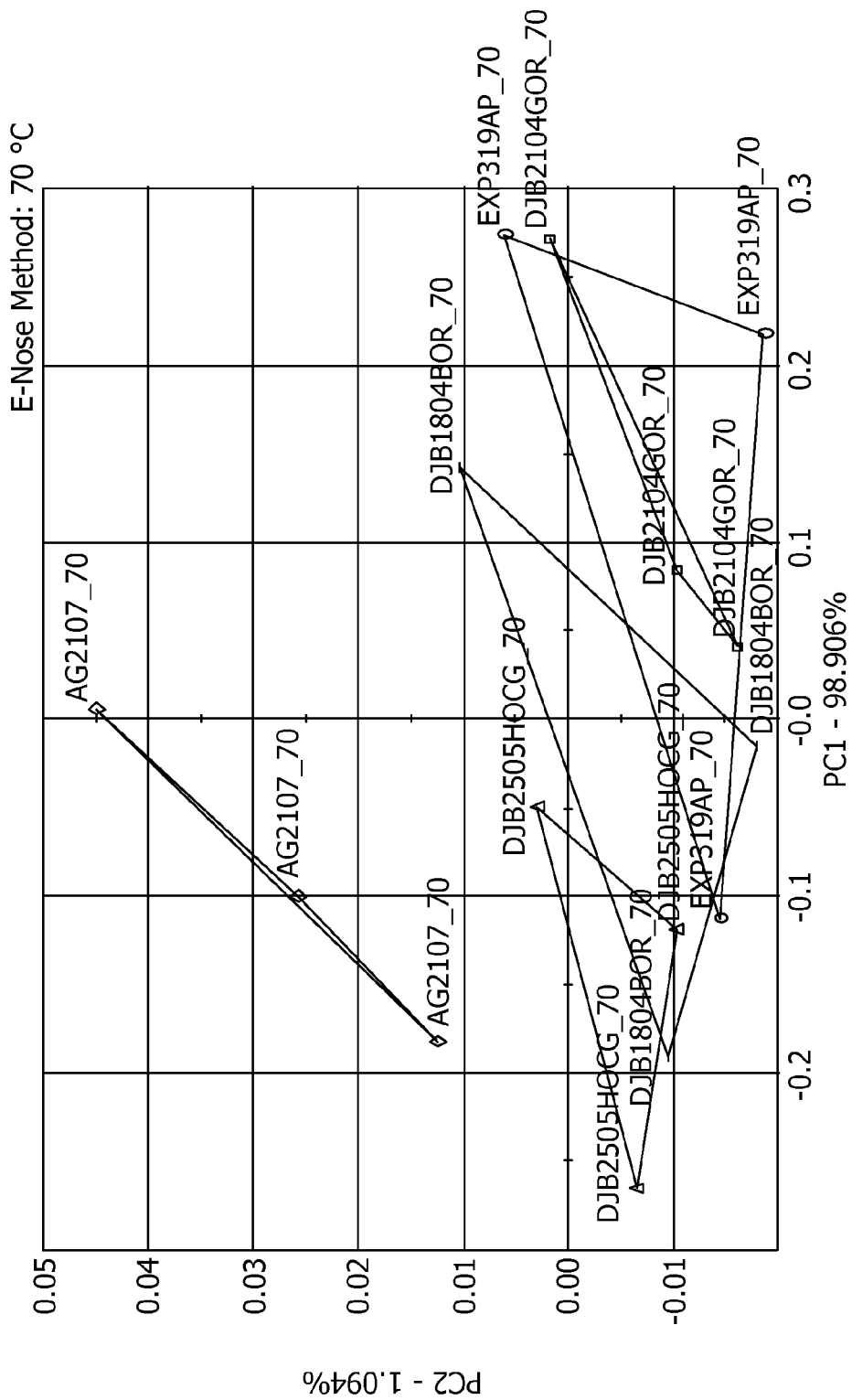
FIG. 5 is a graph of the PCA analysis of a sample of ground soybeans in water heated to 70° C. and analyzed according to Example 2.
Figure 6:
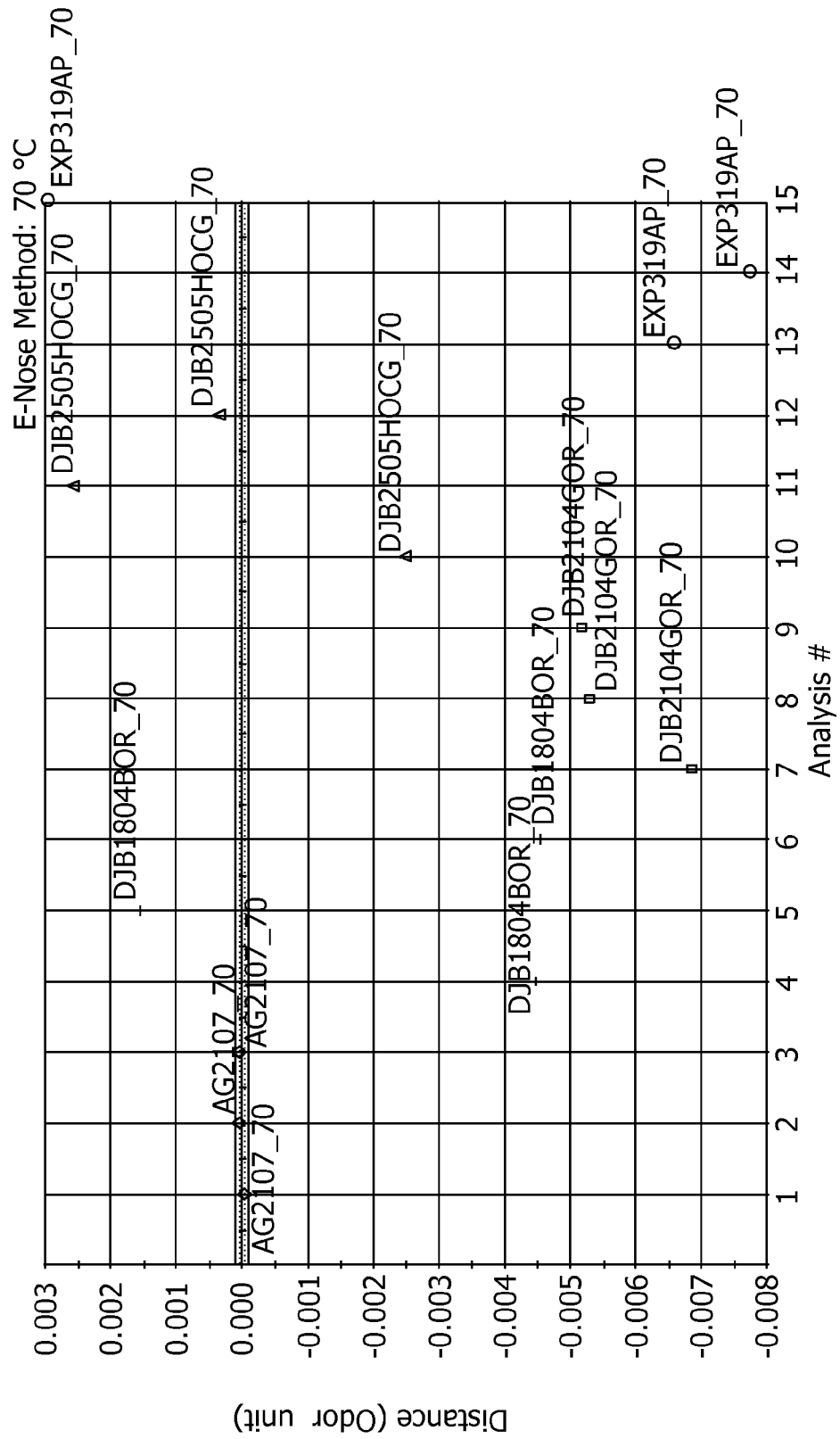
FIG. 6 is a graph of SQC analysis of a sample of ground soybeans in water heated to 70° C. and analyzed according to Example 2.
Figure 7:
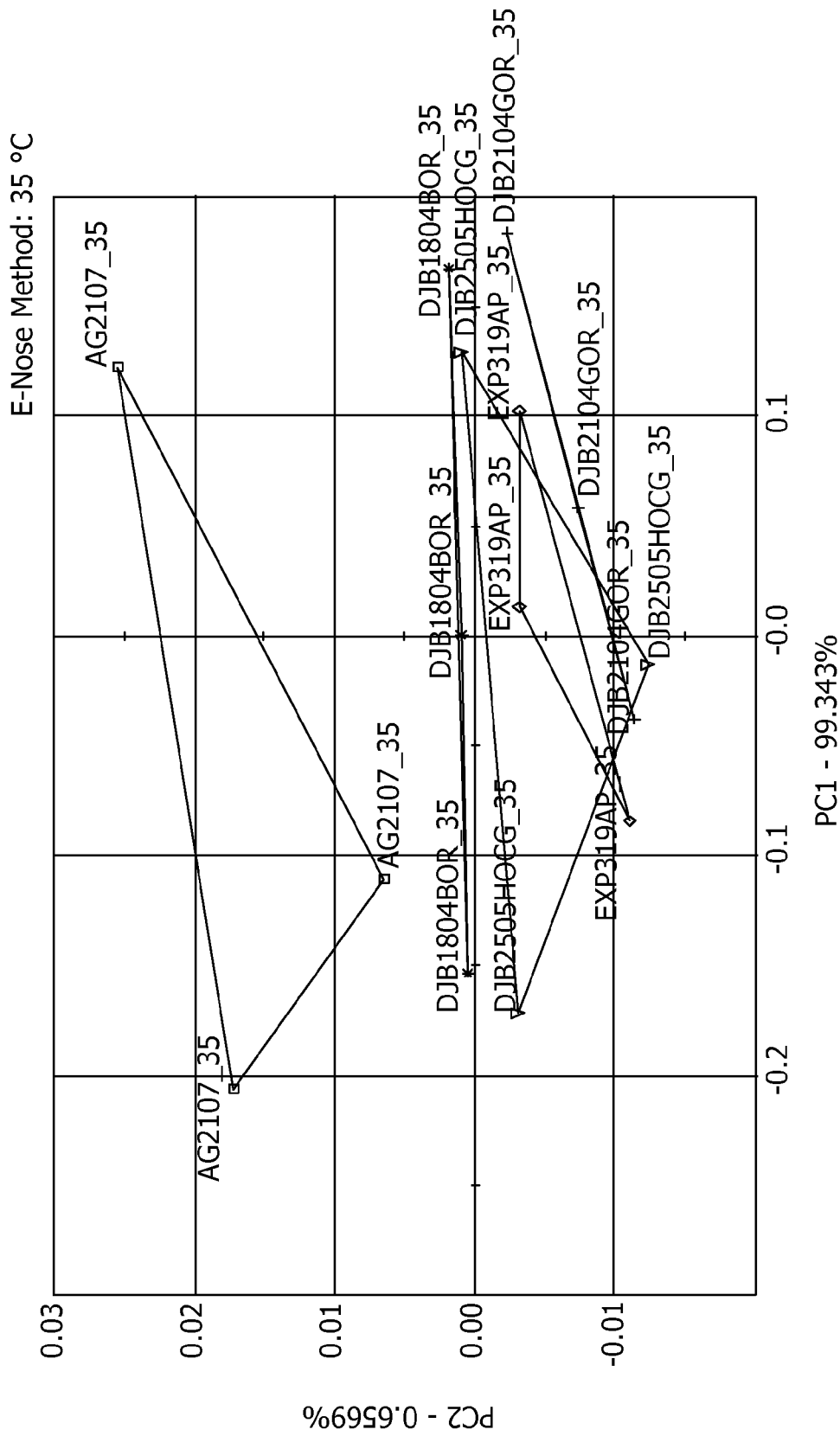
FIG. 7 is a graph of the PCA of a sample of ground soybeans in water heated to 35° C. and analyzed according to Example 2.
Figure 8:
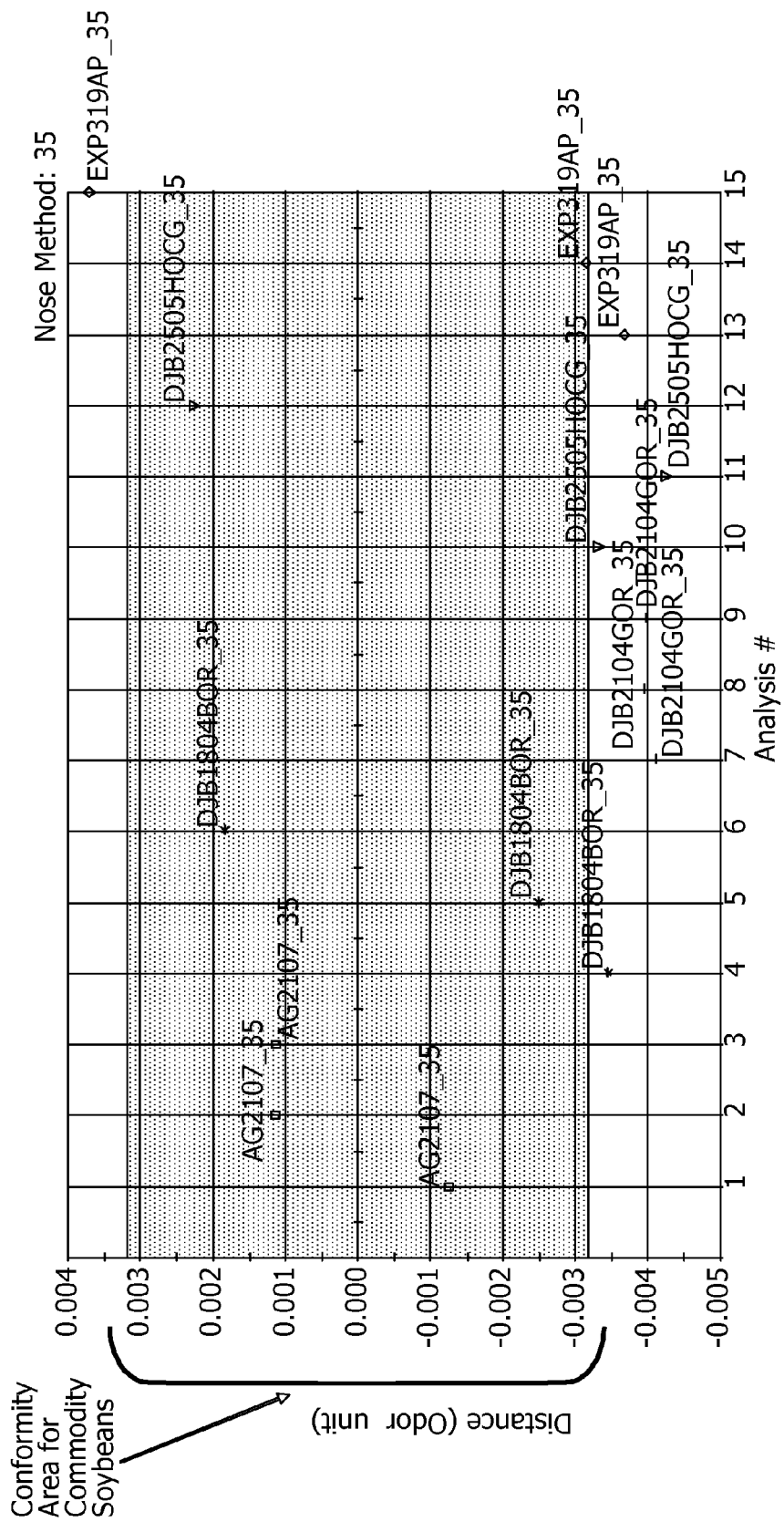
FIG. 8 is a graph of the SQC analysis of a sample of ground soybeans in water heated to 35° C. and analyzed according to Example 2.

Samples of five different varieties of soybeans were obtained. One variety was a typical commodity type soybean and the other three were high β-conglycinin varieties. Three samples of each variety (0.25±0.05 g) were placed in respective 10 ml amber glass vials and 1 ml of water was added to each vial. Each vial was then sealed. One set of the varieties was heated to 35° C. for 20 minutes, one set to 50° C. for 20 minutes and one set to 70° C. for 20 minutes. 2.5 ml of headspace above the sample was injected into a sensor for analysis. The sensor was a Fox 4000 electronic nose system (Alpha MOS; Toulouse, France) using 18 MOS sensing elements. The PCA analysis of the samples heated to 50° C. is shown in FIG. 3 and the SQC analysis of the samples heated to 50° C. is shown in FIG. 4. The principal component analysis of the samples heated to 70° C. is shown in FIG. 5 and the statistical quality control analysis of the samples heated to 70° C. is shown in FIG. 6. The PCA analysis of the samples heated to 35° C. is shown in FIG. 7 and the SQC analysis of the samples heated to 35° C. is shown in FIG. 8. As can be seen from FIGS. 3-6, the commodity soybeans (labeled "AG2107") are grouped separate from the other soybeans which are varieties high in β-conglycinin content (labeled "DJB2505HOCG," "DJB2104GOR," "EXP319AP" and "DJB1804BOR"). This indicates that it is possible to distinguish high β-conglycinin content varieties from other varieties with lower amounts of β-conglycinin and varieties high in aroma from varieties with relatively lower aroma. It was more difficult to distinguish the varieties of soybeans heated to only 35° C. (FIGS. 7-8).

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatus and methods without departing from the scope of the disclosure, it is intended that all matter contained in the above description and shown in the accompanying figures shall be interpreted as illustrative and not in a limiting sense.

What is claimed is:

1. A method for analyzing soybeans, the method comprising:
    grinding the sample of soybeans;
    contacting the ground soybeans with a solvent;
    heating the solvent and ground soybeans to release one or more volatile compounds from the soybeans;
    dissolving the volatile compound in the solvent;
    vaporizing the volatile compound from the solvent;
    sensing the volatile compounds to generate one or more electronic signals; and
    analyzing the one or more electronic signals to determine a characteristic of the soybeans.

2. The method of claim 1 wherein the characteristic is chosen from the group consisting of a β-conglycinin content, genetic line, variety, composition, moisture content, odor intensity, spoilage, gene expression, oil content, fatty acid profile, linoleic acid content, protein content, chlorophyll content, oxidation and combinations thereof.

3. The method of claim 1 wherein the characteristic is β-conglycinin content.

4. The method of claim 1 wherein soybean oil is extracted from a sample of soybeans and the soybean oil is heated to release one or more volatile compounds from the soybeans to determine the fatty acid profile of the soybeans.

5. The method of claim 4 wherein the volatile compounds are analyzed to determine whether the soybeans are a low-linoleic acid variety.

6. The method of claim 1 wherein the characteristic is odor intensity.

7. The method of claim 1 wherein the sample of soybeans is heated to at least 30° C.

8. The method of claim 1 wherein the volatile compounds are sensed by a sensor comprising a sensing element selected from the group consisting of polymers, metal oxides, quartz crystal, surface acoustic wave elements and optical fiber elements.

9. The method of claim 8 wherein the metal oxide is part of a metal oxide semiconductor, the semiconductor being a field-effect transistor.

10. The method of claim 1 wherein the volatile compounds are contacted with an array of sensing elements.

11. The method of claim 1 wherein the electronic signals are analyzed by principal component analysis.

12. The method of claim 1 wherein the electronic signals are analyzed by a statistical quality control model.

13. The method of claim 1 wherein the sample is heated for at least 30 seconds.

14. The method of claim 1 wherein the volatile compounds vaporize into a headspace of a container and a volume of gas in the headspace is injected into the sensor.

15. A method of determining the relative amount of β-conglycinin protein in a sample of soybeans, the method comprising:
   grinding the sample of soybeans;
   contacting the ground soybeans with a solvent;
   heating the solvent and ground soybeans to release one or more volatile compounds from the soybeans;
   dissolving the volatile compound in the solvent;
   vaporizing the volatile compound from the solvent;
   sensing the volatile compounds to generate one or more electronic signals; and
   processing the electronic signals to determine whether the sample of soybeans contains β-conglycinin protein in a concentration greater than commodity soybeans.

16. The method of claim 15 wherein the sample of soybeans is heated to at least 30° C.

17. The method of claim 15 wherein the volatile compounds are sensed by a sensor comprising a sensing element selected from the group consisting of polymers, metal oxides, quartz crystal, surface acoustic wave elements and optical fiber elements.

18. A method of determining the relative intensity of odor of a sample of soybeans, the method comprising:
   grinding the sample of soybeans;
   contacting the ground soybeans with a solvent;
   heating the solvent and ground soybeans to release one or more volatile compounds from the soybeans;
   dissolving the volatile compound in the solvent;
   vaporizing the volatile compound from the solvent;
   sensing the volatile compounds to generate one or more electronic signals; and
   processing the electronic signals to determine whether the sample of soybeans is less odorous than commodity soybeans.

19. The method of claim 18 wherein the sample of soybeans is heated to at least 30° C.

20. The method of claim 18 wherein the volatile compounds are sensed by a sensor comprising a sensing element selected from the group consisting of polymers, metal oxides, quartz crystal, surface acoustic wave elements and optical fiber elements.

* * * * *